United States Patent [19]

Dutra

[11] 4,104,050

[45] Aug. 1, 1978

[54] ACETIMIDIC (α-DIARYLOXYPHOSPHINYLME-THYLAMINO) ACID ESTER HYDROCHLORIDES, HERBICIDAL COMPOSITION AND HERBICIDAL USE THEREOF

[75] Inventor: Gerard A. Dutra, Ladue, Mo.

[73] Assignee: Monsanto Company, St. Louis, Mo.

[21] Appl. No.: 807,953

[22] Filed: Jun. 20, 1977

[51] Int. Cl.$^2$ ............................ A01N 9/36; C07F 9/40
[52] U.S. Cl. ........................................ 71/86; 260/944
[58] Field of Search ............................ 260/944; 71/86

[56] References Cited

U.S. PATENT DOCUMENTS

| | | | |
|---|---|---|---|
| 3,792,130 | 2/1974 | Stach | 260/944 |
| 3,853,530 | 12/1974 | Franz | 71/86 X |
| 3,977,860 | 8/1976 | Franz | 260/944 X |

Primary Examiner—Joseph Paul Brust
Attorney, Agent, or Firm—William T. Black; Donald W. Peterson

[57] ABSTRACT

This disclosure relates to acetimidic acid ester hydrochlorides. More particularly, this disclosure relates to novel (α-diaryloxyphosphinylmethylamino) acetimidic hydrocarbon ester hydrochloride, herbicidal compositions containing such acetimidic hydrochloride and the herbicidal use thereof.

30 Claims, No Drawings

ACETIMIDIC (α-DIARYLOXYPHOSPHINYLMETHYLAMINO) ACID ESTER HYDROCHLORIDES, HERBICIDAL COMPOSITION AND HERBICIDAL USE THEREOF

This invention relates to acetimidic acid ester hydrochlorides. More particularly, this invention relates to novel phosphinylmethylamino substituted acetimidic ester hydrochlorides to novel herbicidal compositions containing the same and to the herbicidal use thereof.

(Diaryloxyphosphinylmethylamino) glycinonitriles are known to be active post-emergent herbicides. These compounds are shown in my copending application Ser. No. 750,327, filed Dec. 13, 1976. It is also known that these compounds can be converted to N-phosphonomethylglycine by hydrolysis with aqueous hydrochloric acid. N-phosphonomethylglycine is an excellent post-emergent herbicide as is known from U.S. Pat. No. 3,799,758 issued Mar. 26, 1974.

It has now been discovered that novel (α-diaryloxyphosphinylmethylamino) acetimidic acid ester hydrochlorides can be produced by the reaction of (diaryloxyphosphinylmethylamino) glycinonitriles with alcohols or phenols and hydrogen chloride under anhydrous conditions employing a solvent.

The novel imidate esters of this invention are those of the formula

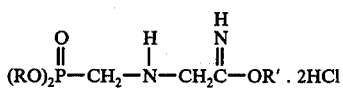

wherein R is phenyl, biphenyl, naphthyl or a lower alkyl substituted phenyl or naphthyl group and R' is a primary or secondary alkyl group containing from 2 to 10 carbon atoms, a cycloalkyl or lower alkyl substituted cycloalkyl group in which the cycloalkyl group contains 5 to 7 carbon atoms, a phenyl group or lower alkyl, lower alkoxy or chloro-substituted phenyl group.

The lower alkyl as employed herein means alkyl groups containing 1 to 4 carbon atoms. Illustrative of the lower alkyl substituted phenyl and naphthyl groups which R represents include o-, m- and p-tolyl, xylyl, mesityl, ethylphenyl, isopropylphenyl, butylphenyl, α- and β-methylnaphthyl, α- and β-ethylnaphthyl and the like.

The groups represented by R' include primary and secondary alkyl groups containing from 2 to 10 carbon atoms such as ethyl, propyl, isopropyl, butyl, sec-butyl, pentyl, neo-pentyl, hexyl, 2-ethylhexyl, decyl and cycloalkyl groups such as cyclopentyl, methylcyclopentyl, ethylcyclopentyl, cyclohexyl, methylcyclohexyl and cycloheptyl. Illustrations of the substituted phenyl groups represented by R' are tolyl, ethylphenyl, isopropylphenyl, methoxyphenyl, ethoxyphenyl, halophenyl such as chlorophenyl, p-bromophenyl and fluorophenyl.

In general, the compounds of this invention are prepared by the reaction of a cyanomethylaminomethylphosphonic acid ester of the formula

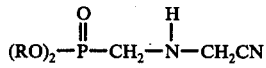

wherein R is as above-defined with an alcohol of the formula R'-OH wherein R' is as above-defined and hydrogen chloride under anhydrous conditions employing methylene chloride as the solvent at a temperature of from about −10° to +10° C. The imidate ester hydrochloride is recovered when it crystallizes out of solution or is precipitated by adding anhydrous diethylether to the reaction mixture.

The compounds of this invention are sensitive to heat and moisture and should, therefore, be stored under anhydrous conditions in a cool place.

The starting cyanomethylaminomethylphosphonic acid esters are prepared by reacting a diaryl phosphite such as diphenyl, ditolyl, dixylyl, di(biphenyl) or di-naphthyl phosphite with s-tri(cyanomethyl)hexahydrotriazine.

The novel (α-diaryloxyphosphinylmethylamino) acetimidic acid ester hydrochlorides of this invention are useful as pre- and post-emergent herbicides.

The following examples serve to further illustrate this invention, all parts being by weight unless otherwise expressly set forth.

EXAMPLE 1

Diphenyl N-phosphonomethylglycinonitrile (1.51 g, 5 mmol) was dissolved in methylene chloride (40 ml), ethanol (0.23 g, 5 mmol) in methylene chloride (10 ml) was added, the mixture was cooled to 0° to −5° C. and dry hydrogen chloride was bubbled in for 2 ½ hours. A solid product crystallized from the methylene chloride and was collected. The solid product was washed with methylene chloride, and yielded 1.78 g of a white solid identified as (α-diphenylphosphinylmethylamino) acetimidic acid ethyl ester dihydrochloride, mp 159°-160° C., which gave the following analysis.

Anal. Calc'd. for $C_{17}H_{23}Cl_2N_2O_4P_1$: C, 48.47; H, 5.50; N, 6.65; Cl, 16.83. Found: C, 48.22; H, 5.55; N, 6.60; Cl, 16.84, 16.91.

EXAMPLE 2

Diphenyl N-phosphonomethylglycinonitrile (0.015 mol, 4.53 g) and freshly distilled p-cresol (0.045 mol, 4.9 g) were dissolved and magnetically stirred in ~200 ml anhydrous methylene chloride under an atmosphere of nitrogen. The 250 ml flask containing the solution was placed in a bath at −1° C. Dry HCl was bubbled through the reaction mixture for 4 hours. Solid formed overnight and was collected by suction filtration to yield 2.3 g (32% yield) of a hygroscopic white solid identified as (60 -diphenoxyphosphinylmethylamino) acetimidic acid p-tolyl ester dihydrochloride which gave the following analysis.

Anal. Calc'd. for $C_{22}H_{25}N_2Cl_2O_4P_1$: C, 54.62; H, 5.21; N, 5.80; Cl, 14.67. Found: C, 54.44; H, 5.29; N, 5.90; Cl, 14.53.

EXAMPLE 3

Diphenyl N-phosphonomethylglycinonitrile (0.015 mol, 4.53 g) and anhydrous isopropanol (0.045 mol, 2.7 g) were dissolved and stirred magnetically in ~200 ml anhydrous methylene chloride under an atmosphere of nitrogen. The reaction flask was placed in a −1° C. bath and dry HCl added over 3.5 hours. Solids formed overnight and which were collected by suction filtration. The solid was washed with cold methylene chloride and ether to yield 5.0 g (77% yield) of a white solid identified as (α-diphenoxyphosphinylmethylamino) acetimidic acid isopropyl ester, dihydrochloride having a melting point of 150°–157° C. with decomposition and which gave the following analysis.

Calculated: C, 49.67; H, 5.79; N, 6.44; Cl, 16.29.
Found: C, 49.66; H, 5.84; N, 6.33; Cl, 16.16.

EXAMPLE 4

Diphenyl N-phosphonomethylglycinonitrile (0.030 mol, 9.07 g) and p-methoxyphenol (0.090 mol, 11.2 g) were dissolved and stirred magnetically in ~300 ml anhydrous methylene chloride under an atmosphere of nitrogen. The reaction vessel was placed into a bath at −1° C. Dry HCl was bubbled through the reaction mixture for 2.5 hours. Solids formed overnight and were collected by suction filtration and washed with methylene chloride and ether to yield 13.11 g (88% yield) of a hygroscopic white solid, mp 128–137° C. with decomposition identified as ($\alpha$-diphenoxyphosphinylmethylamino) acetimidic acid p-methoxyphenyl ester dihydrochloride having the following analysis.

Calculated: C, 52.92; H, 5.05; N, 5.61; Cl, 14.20.
Found: C, 52.72; H, 5.13; N, 5.54; Cl, 14.09.

EXAMPLE 5

Diphenyl N-phosphonomethylglycinonitrile (0.030 mol, 9.07 g) and freshly distilled isopentyl alcohol (0.090 mol, 7.9 g) were magnetically stirred in ~350 ml anhydrous methylene chloride under an atmosphere of nitrogen. The reaction vessel was placed in an ~0° C. bath. Dry HCl was bubbled through the reaction mixture for 3.5 hours. White solid formed and was collected by suction filtration followed by a methylene chloride and an ether wash to yield 8.76 g (62% yield) of a slightly hygroscopic solid, mp 155°–160° C. with decomposition identified as ($\alpha$-diphenoxyphosphinylmethylamino) acetimidic acid isopentyl ester dihydrochloride. The compound had the following analysis.

Calculated: C, 51.84; H, 6.31; N, 6.05; Cl, 15.30.
Found: C, 51.62; H, 6.35; N, 6.04; Cl, 15.17.

EXAMPLE 6

Diphenyl N-phosphonomethylglycinonitrile (0.030 mol, 9.07 g) and p-chlorophenol (0.090 mol, 11.6 g) (purified by sublimation) was mixed in ~350 ml anhydrous methylene chloride and stirred magnetically under an atmosphere of nitrogen. The reaction vessel was placed in a −1° C. bath and dry HCl addition to the reaction lasted 2 hours. Solids formed overnight and were collected by suction filtration followed by a cold methylene chloride and ether wash to yield 1.77 g (12% yield) of a very hygroscopic white solid which was identified as ($\alpha$-diphenoxyphosphinylmethylamino) acetimidic acid p-chlorophenyl ester dihydrochloride and had the following analysis.

Calculated: C, 50.07; H, 4.40; N, 5.56; Cl, 21.11.
Found: C, 49.85; H, 4.52; N, 5.71; Cl, 20.89.

EXAMPLE 7

A methylene chloride solution (300 ml) of diphenyl N-phosphonomethylglycinonitrile (9.07 g, 30 mmol) and 1-octanol (7.8 g, 60 mmol) was cooled to 0° C. and dry hydrogen chloride added over 3 hours. After the addition stopped, no crystallization occurred. Ether was added (10 ml) and the product crystallized out of solution on standing at 0° C. overnight. The product was filtered, washed with methylene chloride then ether and dried with nitrogen to give 2.5–13 g (18–88%) of a white solid identified as ($\alpha$-diphenoxyphosphinylmethylamino) acetimidic acid octyl ester dihydrochloride having a melting point of 156°–159° C.

EXAMPLE 8

A methylene chloride solution (300 ml) of diphenyl N-phosphonomethylglycinonitrile (9.07 g, 30 mmol) and cyclohexanol (6.01 g, 60 mmol) was cooled to 0° C. and dry hydrogen chloride added over 3 hours. After the addition stopped, the product crystallized out of the solution, was filtered, washed with methylene chloride and dried with nitrogen to give 7.0 g (50%) of a white solid identified as ($\alpha$-diphenoxyphosphinylmethylamino) acetimidic acid cyclohexyl ester dihydrochloride and having a melting point of 170°–173° C.

EXAMPLE 9

Diphenyl N-phosphonomethylglycinonitrile (6.04 g, 0.02 mol), neo-pentyl alcohol (1.76 g, 0.02 mol) and methylene chloride (100 ml) was charged into an oven-dried 250 ml three-necked flask equipped with a nitrogen inlet tube, magnetic stirring bar and thermometer after cooling under a nitrogen sparge. The resulting clear solution was cooled to −5° C. and anhydrous hydrogen chloride bubbled through the solution for 2 hours. The reaction mixture was maintained at −5° C. for 48 hours with stirring. Diethyl ether (10 ml) was then added and a precipitate formed. After 1 hour, the mixture was filtered under nitrogen to yield a white solid identified as ($\alpha$-diphenoxyphosphinylmethylamino) acetimidic acid neo-pentyl ester dihydrochloride (7.3 g, 0.0158 mol, 96%) having a melting point of 73°–82° C. and the following analysis.

Calculated: C, 51.84; H, 6.31; N, 6.05; Cl, 15.30.
Found : C, 51.63; H, 6.30; N, 6.08; Cl, 15.24.

EXAMPLE 10

The post-emergent herbicidal activity of the compounds of this invention is demonstrated as follows. The active ingredients are applied in spray form to 14 or 21 day old specimens of the various plant species. The spray, a water solution containing the active ingredient and a surfactant (35 parts butylamine salt of dodecylbenzene sulfonic acid and 65 parts tall oil condensed with ethylene oxide in the ratio of 11 moles ethylene oxide to 1 mole tall oil) is applied to the plants in different sets of pans at several rates (kilograms of active ingredient per hectare), normally at 306 liters/hectare spray volume. In the tables, the examples with letters appearing after the number were prepared in solvents, either anhydrous ethanol (a), acetone (c) or dimethylformamide (d), or tetrahydrofuran (b). The treated plants are placed in a greenhouse and the effects are observed and recorded after approximately 2 or 4 weeks (WAT) as is indicated in the table.

The post-emergence herbicidal index used in the table is as follows:

```
0 = 0 to 24% control
1 = 25 to 49% control
2 = 50 to 74% control
3 = 75 to 99% control
4 = 100% kill
```

The plant species employed in the table are as follows:

```
A - Canada Thistle      K - Barnyard Grass
B - Cocklebur           L - Soybean
```

-continued

| | |
|---|---|
| C - Velvet Leaf | M - Sugar Beet |
| D - Morning Glory | N - Wheat |
| E - Lambsquarters | O - Rice |
| F - Smartweed | P - Sorghum |
| G - Nutsedge | Q - Wild Buckwheat |
| H - Quackgrass | R - Hemp Sesbania |
| I - Johnson Grass | S - Panicum Spp |
| J - Downy Brome | T - Crabgrass |

Table I

| Compound of Example | WAT | kg/h | A | B | C | D | E | F | G | H | I | J | K |
|---|---|---|---|---|---|---|---|---|---|---|---|---|---|
| 1 | 4 | 11.2 | 4 | 4 | 4 | 4 | 4 | 4 | 3 | 4 | 4 | 4 | 4 |
| 1 | 4 | 4.48 | 2 | 4 | 4 | 4 | 4 | 4 | 3 | 4 | 4 | 3 | 4 |
| 1 (c)** | 4 | 11.2 | 1 | 4 | 4 | 4 | 4 | 3 | 2 | 2 | 4 | 3 | 4 |
| 1 (c)** | 4 | 4.48 | 2 | 4 | 3 | 3 | 3 | — | 1 | 1 | 2 | 1 | 3 |
| 1 | 4 | 5.60 | 4 | 4 | 4 | 3 | 4 | 4 | 4 | 4 | 4 | 3 | 4 |
| 1 (a) | 4 | 5.60 | 4 | 4 | 3 | 4 | 4 | 4 | 3 | 4 | 3 | 4 | 4 |
| 1 (d) | 4 | 5.60 | 4 | 3 | 3 | 2 | 4 | 4 | 3 | 4 | 4 | 4 | 4 |
| 1 (a)** | 4 | 5.60 | 4 | 4 | 4 | 4 | 4 | 4 | 2 | 4 | 4 | 4 | 3 |
| 1* | 4 | 5.60 | 4 | 4 | 4 | 4 | 4 | 4 | 3 | 4 | 4 | 4 | 4 |
| 1 (a)* | 4 | 5.60 | 2 | 3 | 3 | 2 | 4 | 4 | 2 | 4 | 4 | 4 | 4 |
| 2 | 4 | 11.2 | 4 | 4 | 3 | 2 | 4 | 4 | 2 | 2 | 4 | 3 | 4 |
| 2 | 4 | 5.60 | 3 | 3 | 2 | 2 | 4 | 3 | 2 | 3 | 3 | 4 | 4 |
| 2 (a) | 4 | 11.2 | 3 | 4 | 3 | 2 | 4 | 4 | 2 | 2 | 3 | 3 | 4 |
| 2 (a) | 4 | 5.60 | 2 | 3 | 2 | 2 | 4 | 3 | 1 | 1 | 2 | 1 | 3 |
| 3 | 4 | 11.2 | 1 | 3 | 3 | 2 | 3 | 4 | 3 | 3 | 3 | 4 | 4 |
| 3 | 4 | 5.60 | 3 | 3 | 2 | 2 | 4 | 4 | 2 | 3 | 3 | 4 | 4 |
| 3 (a) | 4 | 11.2 | 2 | 3 | 3 | 2 | 4 | 4 | 3 | 4 | 3 | 4 | 4 |
| 3 (a) | 4 | 5.60 | 1 | 2 | 1 | 2 | 4 | 4 | 2 | 3 | 3 | 4 | 4 |
| 4 | 4 | 11.2 | 4 | 4 | 2 | 4 | 4 | 4 | 3 | 4 | 4 | 4 | 3 |
| 4 | 4 | 5.60 | 4 | 4 | 2 | 2 | 4 | 4 | 3 | 4 | 3 | 4 | 3 |
| 4 (a) | 4 | 11.2 | 4 | 4 | 3 | 3 | 4 | 4 | 3 | 4 | 4 | 4 | 4 |
| 4 (a) | 4 | 5.60 | 4 | 4 | 2 | 4 | 4 | 4 | 3 | 4 | 4 | 4 | 3 |
| 5 | 4 | 11.2 | 3 | 3 | 2 | 4 | 4 | 4 | 3 | 2 | 2 | 4 | 4 |
| 5 | 4 | 5.60 | 2 | 3 | 3 | 4 | 4 | 4 | 2 | 4 | 2 | 4 | 3 |
| 7 (b) | 4 | 11.2 | 2 | 2 | 1 | 2 | 4 | 4 | 2 | 4 | 3 | 1 | 3 |
| 7 (b) | 4 | 5.60 | 4 | 2 | 1 | 1 | 4 | 4 | 2 | 3 | 3 | 2 | 3 |
| 8 | 4 | 11.2 | 1 | 2 | 1 | 1 | 3 | 4 | 2 | 3 | 3 | 2 | 3 |
| 8 | 4 | 5.60 | 1 | 2 | 1 | 1 | 4 | 3 | 2 | 4 | 3 | 3 | 3 |
| 9 | 4 | 11.2 | 2 | 2 | 3 | 2 | 4 | 4 | 1 | 2 | 4 | 3 | 4 |
| 9 | 4 | 5.60 | 2 | 2 | 4 | 3 | 4 | 4 | 2 | 1 | 4 | 3 | 3 |

*spray volume 77 liters/hectare
**spray volume 153 liters/hectare

Table II

| Compound of Example | WAT | kg/h | L | M | N | O | P | B | Q | D | R | E | F | C | J | S | K | T |
|---|---|---|---|---|---|---|---|---|---|---|---|---|---|---|---|---|---|---|
| 1 | 4 | 4.48 | 4 | 4 | 4 | 3 | 3 | 4 | 3 | 4 | 3 | 3 | 3 | 4 | 2 | 4 | 4 | 4 |
| 1 | 4 | 1.12 | 2 | 4 | 2 | 2 | 3 | — | 1 | 3 | 3 | 3 | 3 | 3 | 2 | 4 | 3 | 3 |
| 1 | 4 | .224 | 1 | — | 0 | 0 | 1 | — | 0 | 1 | 1 | 0 | 1 | 0 | 0 | 2 | 1 | 1 |
| 1 | 4 | .112 | 1 | 4 | 0 | 0 | 1 | 1 | 0 | 1 | 1 | 1 | 1 | 0 | 0 | 2 | 0 | 1 |
| 2 | 4 | 5.60 | 2 | 3 | 3 | 1 | 3 | 3 | 1 | 2 | 1 | 3 | 4 | 1 | 3 | 3 | 4 | 4 |
| 2 | 4 | 1.12 | 2 | 2 | 1 | 1 | 3 | 2 | 1 | 2 | 1 | 1 | — | 1 | 2 | 2 | 2 | 2 |
| 2 | 4 | .280 | 1 | 1 | 0 | 0 | 2 | 1 | 1 | 1 | 0 | 0 | — | 0 | 0 | 1 | 1 | 2 |
| 2 (a) | 4 | 5.60 | 3 | 3 | 2 | 1 | 3 | 3 | 1 | 2 | 1 | 2 | — | 2 | 4 | 4 | 3 | 3 |
| 2 (a) | 4 | 1.12 | 2 | 1 | 1 | 1 | 2 | 2 | 1 | 1 | 1 | 2 | — | 1 | 1 | 3 | 3 | 3 |
| 2 (a) | 4 | .280 | 1 | 0 | 1 | 0 | 1 | 1 | 0 | 1 | 0 | 0 | — | 0 | — | 1 | 1 | 1 |
| 3 | 4 | 5.60 | 3 | 4 | 3 | 3 | 4 | 3 | 4 | 2 | 2 | 3 | 4 | 3 | 4 | 4 | 3 | 4 |
| 3 | 4 | 1.12 | 2 | 2 | 2 | 2 | 4 | 2 | 1 | 2 | 2 | 2 | 3 | 1 | 1 | 3 | 2 | 3 |
| 3 | 4 | .280 | 1 | 1 | 1 | 1 | 2 | 1 | 0 | 1 | 0 | 1 | 1 | 1 | 0 | 2 | 1 | 2 |
| 3 (a) | 4 | 5.60 | 2 | 3 | 4 | 4 | 4 | 3 | 3 | 2 | 2 | 2 | 4 | 3 | 3 | 4 | 3 | 4 |
| 3 (a) | 4 | 1.12 | 1 | 1 | 2 | 1 | 3 | 2 | 1 | 1 | 0 | 1 | 2 | 1 | 1 | 2 | 2 | 2 |
| 3 (a) | 4 | .280 | 0 | 0 | 0 | 0 | 1 | 1 | 1 | 1 | 0 | 1 | 1 | 1 | 0 | 2 | 1 | 2 |
| 4 | 4 | 5.60 | 4 | 4 | 4 | 2 | 4 | 4 | 4 | 4 | 4 | 4 | 4 | 4 | 4 | 4 | 4 | 3 |
| 4 | 4 | 1.12 | 2 | 3 | 4 | 1 | 3 | 3 | 3 | 2 | 2 | 4 | 4 | 3 | 4 | 4 | 4 | 4 |
| 4 | 4 | .280 | 1 | 1 | 1 | 1 | 2 | 1 | 1 | 2 | 1 | 2 | 2 | 1 | 2 | 3 | 3 | 3 |
| 4 (a) | 4 | 5.60 | 4 | 4 | 4 | 2 | 4 | 4 | 2 | 4 | 3 | 4 | 4 | 4 | 4 | 4 | 4 | 3 |
| 4 (a) | 4 | 1.12 | 2 | 3 | 3 | 2 | 3 | 3 | 2 | 2 | 3 | 4 | 3 | 3 | 3 | 3 | 3 | 4 |
| 4 (a) | 4 | .280 | 1 | 3 | 1 | 1 | 2 | 2 | 2 | 2 | 2 | 3 | 3 | 1 | 2 | 4 | 3 | 3 |
| 5 | 4 | 5.60 | 4 | 4 | 4 | 4 | 4 | 3 | 2 | 4 | 2 | 4 | 4 | 4 | 4 | 4 | 4 | 4 |
| 5 | 4 | 1.12 | 2 | 4 | 4 | 2 | 4 | 4 | 2 | 3 | 2 | 4 | 4 | 3 | 4 | 4 | 4 | 4 |
| 5 | 4 | .280 | 1 | 1 | 2 | 1 | 3 | 2 | 1 | 2 | 1 | 2 | 2 | 2 | 3 | 3 | 3 | 3 |
| 5 (b) | 4 | .056 | 0 | 2 | 0 | 0 | 1 | 1 | 1 | 2 | 0 | 4 | 0 | 2 | 0 | 1 | 0 | 1 |
| 7 (b) | 4 | 5.60 | 2 | 4 | 3 | 2 | 3 | 3 | 2 | 2 | 4 | 4 | 4 | 4 | 3 | 4 | 3 | 4 |
| 7 (b) | 4 | 1.12 | 1 | 2 | 1 | 2 | 2 | 1 | 1 | 2 | 2 | 4 | 2 | 2 | 3 | 3 | 2 | 3 |
| 7 (b) | 4 | .280 | 1 | 1 | 0 | 0 | 2 | 2 | 0 | 1 | 1 | 2 | 2 | 2 | 1 | 2 | 1 | 3 |
| 7 (b) | 4 | .056 | 1 | 1 | 0 | 0 | 1 | 1 | 0 | 1 | 1 | 1 | 1 | 1 | 0 | 2 | 1 | 1 |
| 8 | 4 | 5.60 | 2 | 3 | 4 | 2 | 3 | 2 | 2 | 2 | 2 | 4 | 3 | 3 | 4 | 3 | 4 | 4 |
| 8 | 4 | 1.12 | 1 | 1 | 2 | 1 | 2 | 1 | 1 | 1 | 2 | 3 | 1 | 1 | 3 | 2 | 1 | 4 |
| 8 | 4 | .280 | 0 | 0 | 0 | 0 | 1 | 0 | 1 | 1 | 0 | 1 | 1 | 0 | 0 | 1 | 1 | 3 |
| 9 | 4 | 5.60 | 3 | 3 | 4 | 4 | 3 | 2 | 3 | 3 | 4 | 4 | 3 | 3 | 4 | 4 | 4 | 4 |
| 9 | 4 | 1.12 | 1 | 4 | 1 | 1 | 3 | 1 | 4 | 3 | 2 | 2 | 2 | 1 | 2 | 4 | 3 | 3 |
| 9 | 4 | .280 | 0 | 1 | 0 | 0 | 2 | 0 | 1 | 0 | 0 | 0 | 0 | 0 | 0 | 3 | 2 | 1 |
| 9 | 2 | .056 | 0 | 0 | 0 | 0 | 0 | 0 | 0 | 1 | 0 | 0 | 0 | 0 | 0 | 0 | 0 | 0 |

EXAMPLE 11

This example illustrates pre-emergent activity of the compounds of this invention.

A good grade of top soil is placed in aluminum pans and compacted to a depth of ⅜ to ½ inch from the top of each pan. A pre-determined number of seeds and vegetative propagules of each of several plant species are placed on top of the soil in the pans. The seeds and propagules are covered with a measured amount of soil containing the chemical admixed throughout. The herbicidal composition is applied at the rate indicated by spraying the soil to be used as a cover layer, then thoroughly mixing the soil and herbicidal compound. The pans are placed on the sand of a greenhouse bench and watered as needed. The soil in the pans absorbs moisture through the apertured bottom of the pans. The plants are observed at the end of approximately 2 or 4 weeks (WAT) and the results recorded.

The pre-emergent herbicidal activity of the compounds of this invention is measured by the average percent control of each of the plant species. The average percent control is converted to a relative numerical scale for the sake of brevity and simplicity in the example. The pre-emergent herbicidal activity index used in the table is defined as follows:

Table III

0 = 0 to 24% control
1 = 25 to 49% control
2 = 50 to 74% control
3 = 75 to 100% control

| Compound of Example | WAT | kg/h | Plant Species | | | | | | | | | | |
|---|---|---|---|---|---|---|---|---|---|---|---|---|---|
| | | | A | B | C | D | E | F | G | H | I | J | K |
| 1 | 4 | 11.2 | 2 | 0 | 0 | 0 | 0 | 0 | 0 | 0 | 3 | 0 | 0 |
| 2 | 2 | 11.2 | 3 | 0 | 0 | 0 | 3 | 0 | 0 | 0 | 0 | 0 | 0 |
| 2 (a) | 2 | 11.2 | 3 | 0 | 0 | 0 | 0 | 0 | 0 | 0 | 0 | 0 | 0 |
| 3 | 2 | 11.2 | 1 | 0 | 0 | 0 | 0 | 0 | 1 | 1 | 1 | 0 | 0 |
| 3 (a) | 2 | 11.2 | 1 | 0 | 0 | 0 | 0 | 0 | 0 | 0 | 0 | 0 | 0 |
| 4 | 2 | 11.2 | 0 | 0 | 0 | 0 | 0 | 0 | 0 | 0 | 0 | 0 | 0 |
| 4 (a) | 2 | 11.2 | 0 | 0 | 0 | 0 | 0 | 0 | 0 | 0 | 0 | 0 | 0 |
| 5 | 2 | 11.2 | 3 | 0 | 0 | 0 | 0 | 0 | 0 | 2 | 0 | 0 | 0 |
| 7 (b) | 2 | 11.2 | 3 | 0 | 0 | 0 | 0 | 0 | 0 | 0 | 0 | 0 | 0 |
| 8 | 4 | 11.2 | 0 | 0 | 0 | 0 | 0 | 0 | 0 | 2 | 1 | 0 | 1 |
| 9 | 2 | 11.2 | 0 | 0 | 0 | 0 | 0 | 0 | 0 | 2 | 0 | 0 | 0 |

For the sake of brevity and simplicity, the term "active ingredient" is employed hereinafter in this specification to describe the acetimidic (α-diaryloxyphosphinylmethylamino) acid ester hydrochloride derivatives of this invention, hereinbefore described.

In herbicidal compositions, the active ingredient can be admixed with one or more adjuvants which can be solid or liquid extenders, carriers, diluents (preferably which do not react with the acetimidic esters), conditioning agents and the like. The herbicidal formulations comprise wettable powders, aqueous suspensions, dust formulations, emulsifiable oils and solutions in solvents. In general, these formulations can all contain one or more surface-active agents.

Surface-active agents which can be used in herbicidal formulations are well known to those skilled in the art and have been well documented in U.S. patents, bulletins and textbooks.

The preparation, formulations and particle size of the wettable powders, aqueous suspensions, dusts, emulsifiable oils and solutions in solvents are also well known to those skilled in the art and well documented.

The active ingredient is usually present in the herbicidal compositions in a range of about 0.5 to 95 parts by weight per 100 parts by weight of wettable or soluble powder, or wettable dust formulations; 5 to 95 parts by weight per 100 parts by weight emulsifiable oil formulations. A water formulation usually contains from 1 to 95 parts by weight of the active ingredient which can be further diluted for application. Formulations containing other than the above quantities of active ingredient can easily be prepared by those skilled in the art.

Application of the herbicidal compositions of this invention to the plant is well known to those skilled in the art. The application of liquid and particulate solid herbicidal formulations to the above-ground portions of the plants can be carried out by conventional methods, e.g., power dusters, boom and hand sprayers and spray dusters, however, since most of the compositions of this invention are water soluble, it is preferred to apply them in an aqueous medium.

The active ingredient can be admixed with one or more adjuvants which can be solid or liquid extenders, carriers, diluents, conditioning agents and the like to form herbicidal compositions. Herbicidal formulations have been described hereinbefore with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereby by those skilled in the art to which the invention pertains.

What is claimed is:

1. A compound of the formula

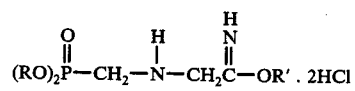

wherein R is phenyl or a lower alkyl substituted phenyl group said lower alkyl containing 1 to 4 carbon atoms and R' is a primary or secondary alkyl group containing 2 to 10 carbon atoms, cyclohexyl, phenyl or a lower alkyl, lower alkoxy or chlorosubstituted phenyl group said lower alkyl and lower alkoxy containing 1 to 4 carbon atoms.

2. A compound of claim 1 wherein R is a phenyl group.

3. A compound of claim 2 wherein R' is ethyl.

4. A compound of claim 2 wherein R' is isopropyl.

5. A compound of claim 2 wherein R' is cyclohexyl.

6. A compound of claim 2 wherein R' is isopentyl.

7. A compound of claim 2 wherein R' is octyl.

8. A compound of claim 2 wherein R' is p-methylphenyl.

9. A compound of claim 2 wherein R' is neo-pentyl.

10. A compound of claim 2 wherein R' is p-methoxyphenyl.

11. A herbicidal method which comprises applying to plants a herbicidally effective amount of a compound of claim 1.

12. A herbicidal method which comprises applying to plants a herbicidally effective amount of a compound of claim 2.

13. A herbicidal method which comprises applying to plants a herbicidally effective amount of a compound of claim 3.

14. A herbicidal method which comprises applying to plants a herbicidally effective amount of compound of claim 4.

15. A herbicidal method which comprises applying to plants a herbicidally effective amount of a compound of claim 5.

16. A herbicidal method which comprises applying to plants a herbicidally effective amount of a compound of claim 6.

17. A herbicidal method which comprises applying to plants a herbicidally effective amount of a compound of claim 7.

18. A herbicidal method which comprises applying to plants a herbicidally effective amount of a compound of claim 8.

19. A herbicidal method which comprises applying to plants a herbicidally effective amount of a compound of claim 9.

20. A herbicidal method which comprises applying to plants a herbicidally effective amount of a compound of claim 10.

21. A herbicidal composition comprising a herbicidally effective amount of a compound of claim 1 and a herbicidally inert diluent.

22. A herbicidal composition comprising a herbicidally effective amount of a compound of claim 2 and a herbicidally inert diluent.

23. A herbicidal composition comprising a herbicidally effective amount of a compound of claim 3 and a herbicidally inert diluent.

24. A herbicidal composition comprising a herbicidally effective amount of a compound of claim 4 and a herbicidally inert diluent.

25. A herbicidal composition comprising a herbicidally effective amount of a compound of claim 5 and a herbicidally inert diluent.

26. A herbicidal composition comprising a herbicidally effective amount of a compound of claim 6 and a herbicidally inert diluent.

27. A herbicidal composition comprising a herbicidally effective amount of a compound of claim 7 and a herbicidally inert diluent.

28. A herbicidal composition comprising a herbicidally effective amount of a compound of claim 8 and a herbicidally inert diluent.

29. A herbicidal composition comprising a herbicidally effective amount of a compound of claim 9 and a herbicidally inert diluent.

30. A herbicidal composition comprising a herbicidally effective amount of a compound of claim 10 and a herbicidally inert diluent.

* * * * *